United States Patent [19]

Klemm

[11] Patent Number: Plant 7,111

[45] Date of Patent: Jan. 16, 1990

[54] CARNATION NAMED KLEFICARO

[76] Inventor: Siegfried Klemm, Hanfacker 8, D-7000 Stuttgart 50, Fed. Rep. of Germany

[21] Appl. No.: 252,593

[22] Filed: Oct. 3, 1988

[51] Int. Cl.[4] ..... A01H 5/00

[52] U.S. Cl. ..... Plt./70

[58] Field of Search ..... Plt./70

*Primary Examiner*—James R. Feyrer

*Attorney, Agent, or Firm*—Charles W. Rummler

[57] ABSTRACT

A new variety of miniature carnation plant originated as a sport of the hybrid carnation variety 'Klefitoni' (U.S. Plant Pat. No. 6,704) and distinguished as a fast growing plant producing blooms of a light orange color with red spots or small patches on the flower petals, the plant having strong stems, an average height of about 60 cm., and medium broad leaves in a moderate quantity.

1 Drawing Sheet

BACKGROUND OF THE NEW PLANT

This new carnation variety was discovered by me in 1985 as a sport of the carnation variety 'Klefitoni' growing in my nursery at Stuttgart, West Germany, and this sport was selected by me for propagation because of the unusual coloration of its bloom and propagation was done by me and under my direction by means of cuttings at Stuttgart and several successive generations of this plant generated at Stuttgart by means of cuttings have demonstrated clearly that the novel characteristics of this new plant hold true from generation to generation and appear to be firmly fixed. This new variety of carnation is now being propagated by means of cuttings and on a commercial scale at Stuttgart, as well as in Italy and in Israel.

DESCRIPTION OF THE DRAWING

This new miniature carnation plant is illustrated by the accompanying photographic drawing which shows, in full color, a blooming stem and parts thereof, with the color rendition being as nearly true as it is reasonably possible to obtain by conventional, commercial photographic procedures.

DESCRIPTION OF THE NEW PLANT

The following is a detailed description of this new miniature carnation variety as observed on plants grown in my nursery at Stuttgart, West Germany, with color designations according to The R.H.S. Colour Chart published by The Royal Horticultural Society at London, England.

THE PLANT

Origin: Sport.
Parent variety: 'Klefitoni' (U.S. Plant Pat. No. 6,704).
Classification:
- *Botanic.*—*Dianthus caryophyllus.*
- *Commercial.*—Miniature Carnation.

Form: Bush.
Height: About 60 cm. (first flush).
Growth: Upright and sturdy.
Branching character: Normal.
Foliage:
- *Quantity.*—Moderate with about sixteen leaves per stem in summertime.
- *Leaf size.*—Moderate; about 7 cm. long and about 0.8 cm. wide.

- *Leaf shape.*—Oblong with entire margins.
- *Texture.*—Smooth.
- *Color.*—Upper side: Blue Green. Under side: Blue Green.

Ribs: Single and axial.
Petioles: None. The leaf is amplexicaul.

THE BUD

Size: Medium.
- *Diameter.*—About 15 mm. in average.
- *Length.*—About 35 to 40 mm. according to maturity.

Shape: Ovoid.
Rate of opening: Moderate.
Color of petals: When sepals first divide and petals begin to unfurl: Light Orange.
Sepals:
- *Number.*—Five.
- *Character.*—The sepals stand up when the flower opens.
- *Color.*—Inside and outside: Gray-Green.

Calyx:
- *Shape.*—Cylindrical.
- *Size.*—About 15 mm. wide and about 20 mm. long.
- *Splitting.*—The calyx does not split.
- *Aspect.*—Smooth.

Flower stem: as a product of a pinched main stem
- *Length.*—About 40 to 50 cm., depending upon season of growth.
- *Character.*—Strong and erect.
- *Color.*—Gray-Green.

THE FLOWER

Blooming habit: Continuous the year around, all flowering stems being of pinched stem production.
Size of bloom: Medium.
- *Diameter.*—About 45 to 55 mm. according to season.
- *Depth.*—Averaging about 40 mm.

Borne: Singly, after disbudding the flowering stem.
Shape: High center when bloom first opens, becoming near to dome-shaped as the bloom matures.
Petalage:
- *Number of petals.*—About 35 to 42.
- *Form.*—Fan-shaped with serrated margins.
- *Arrangement.*—Imbricated.
- *Texture.*—Soft.
- *Appearance.*—Shiny.

*Color.*—RHS 19-C with red spots or small patches of 67-A.

Flower stem:

*Length.*—About 45 to 60 cm. according to season.

*Color.*—Gray-Green.

*Character.*—Sturdy and upright.

Effect of wet or hot weather: None. This plant is extremely good under outside growing conditions.

Persistence: The bloom stays upright and the petals hang on and dry.

Fragrance: None.

Lasting quality:

*On the plant.*—About fifteen days.

*As a cut flower.*—About twelve days depending on room conditions.

THE REPRODUCTIVE ORGANS

Stamens:

*Arrangement.*—General.

*Anthers.*—Anthers and pollen are rarely present.

Pistil:

*Number.*—One.

THE SEEDS

Fertility: The seeds are fertile.

Shape: Ovoid.

Color at maturity: Green-Brown.

This plant is a fast growing miniature carnation with a blossom in a light orange color with red stripes, the plant having strong stems with green-blue, medium broad leaves. Other than flower color, this variety most nearly resembles the parent plant with respect to growth habit and physical characteristics.

I claim:

1. The new carnation plant, substantially as herein shown and described, characterized by being a fast growing miniature variety having an average plant height of about 60 cm. producing medium sized flowers of a light orange color having red petal markings growing on strong stems having a moderate amount of medium broad, green-blue leaves.

* * * * *

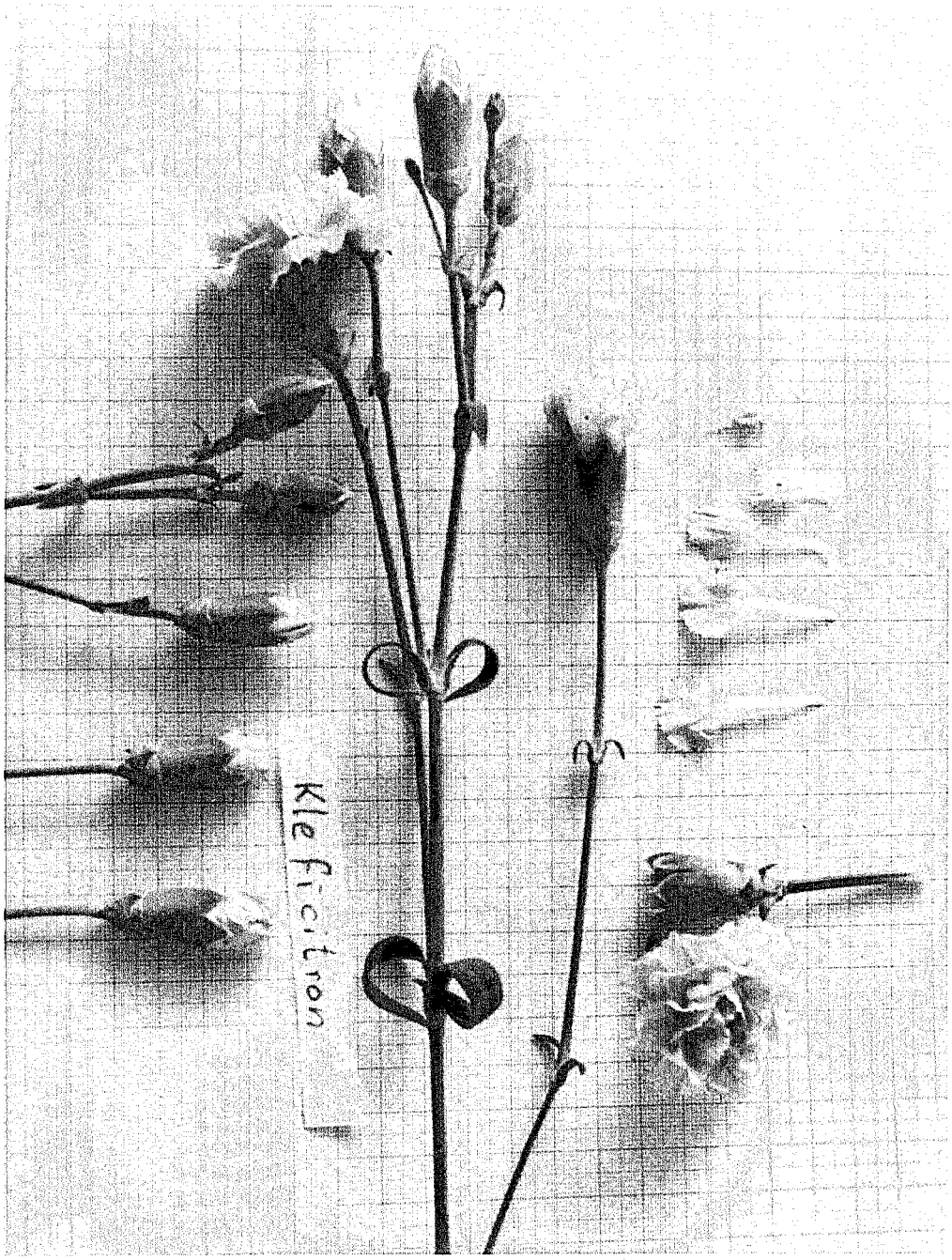
Kle Fic'tron